United States Patent [19]

Jacquet et al.

[11] 4,214,592
[45] Jul. 29, 1980

[54] PATCH FOR SKIN TESTS

[75] Inventors: Pierre Jacquet, Tassin la Demi Lune; Micha Roumiantzeff, Lyons, both of France

[73] Assignee: Institut Merieux, Lyons, France

[21] Appl. No.: 865,511

[22] Filed: Dec. 29, 1977

[30] Foreign Application Priority Data

Dec. 31, 1976 [FR] France .............................. 76 39710

[51] Int. Cl.² .............................................. A61B 10/00
[52] U.S. Cl. ..................................... 128/743; 156/233
[58] Field of Search ............... 128/2 W, 260, 264, 743

[56] References Cited

U.S. PATENT DOCUMENTS

| 2,969,057 | 1/1961 | Simmons | 128/2 W |
|---|---|---|---|
| 3,212,495 | 10/1965 | Osbourn et al. | 128/2 W |
| 3,515,126 | 6/1970 | Fregert | 128/743 |
| 3,894,531 | 7/1975 | Saunders | 128/2 W |
| 4,127,339 | 11/1978 | Malacheski et al. | 128/260 X |

FOREIGN PATENT DOCUMENTS 6710599  2/1968  Netherlands ............. 128/2 W

Primary Examiner—George J. Marlo
Attorney, Agent, or Firm—Norman Lettvin

[57] ABSTRACT

An adhesive patch for skin testing using chemical substances such as dinitrochlorobenzene (DNCB), oxazolone, beryllium fluoride, paraphenylenediamine or other like allergens, the allergen being mixed with an excipient which melts when placed in contact with the skin. The adhesive patch provides a sandwich-type construction that includes an adhesive layer, a first foil layer with one side against the adhesive layer, a layer of liquid impermeable synthetic mterial on the other side of the foil face, an absorbent disc on the synthetic layer, the allergenic material on the absorbent disc and a second foil layer overlying the absorbent disc and forming an air-tight seal with the first foil layer. In use the second foil layer will be removed and the patch adhesively applied to the skin of a user without fear of sensitization of the person handling the patch test.

The patch test is formed by a continuous process wherein a first web of foil that has been covered with a web of synthetic material is advanced longitudinally, separate discs of absorbent material being placed on the synthetic material side of the web at regular intervals as the web is transported longitudinally; the test material diluted in solvent is deposited onto each absorbent disc as same passes a dispensing station, the solvent is evaporated before sealing, and a second web of foil is fed to overlie the first foil web and is then heat-sealed thereto to form discrete pouches in each of which is located an absorbent disc, the sandwiched webs are severed to provide individual units that are then deposited on a web of adhesive patch material in spaced relation, a web of protective material is applied to the adhesive patch material with the spaced units located between said latter two webs, and the further sandwich is severed to produce completed individual units.

17 Claims, 2 Drawing Figures

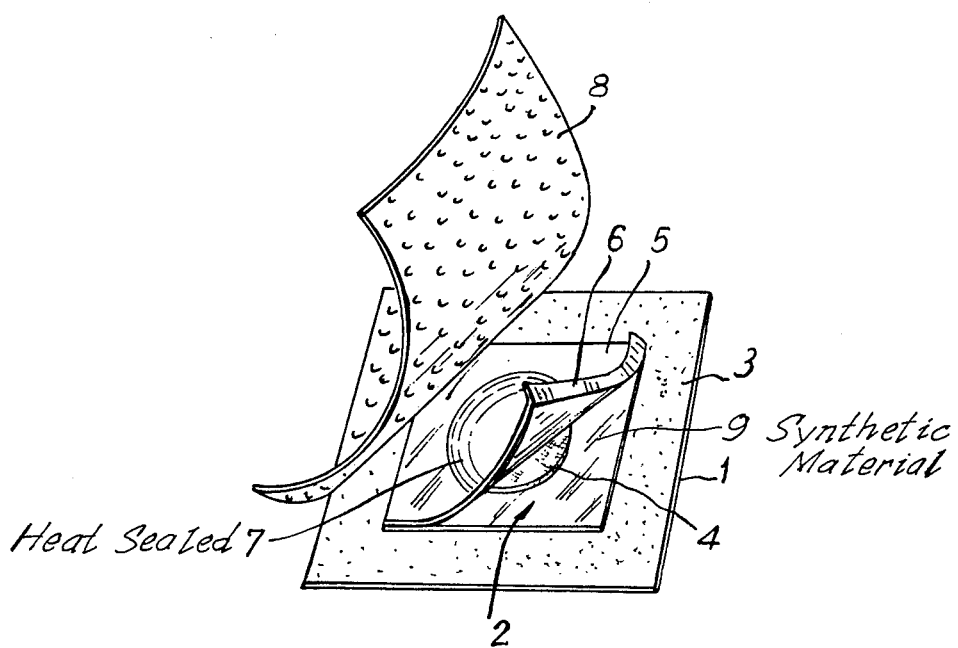
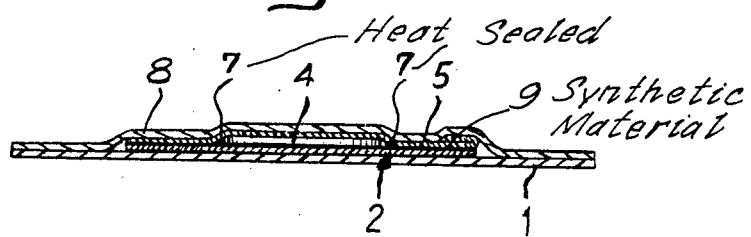

PATCH FOR SKIN TESTS

FIELD OF THE INVENTION

The present invention relates to an adhesive patch for skin tests, as well as to process for the fabrication of said patch.

BACKGROUND OF THE INVENTION

There are already known numerous adhesive patches for skin test referred to as "patch tests", comprising an absorbent patch and an adhesive support, such as for example, a cloth of the "Sparadrap" type, a cloth with adhesive character. At the time of use, the operator puts on the absorbent part a test liquid, following which the patch is applied to the skin, for example, on the arm or on the back of the patient.

The presently known devices present numerous drawbacks. First of all, the test substances used, especially the allergens such as dinitrochlorobenzene present serious dangers of sensitizing for the persons frequently exposed to their contact, which is the base for the operators which must place the substance on the absorbent part, at the time of application of the patch test. These drawbacks are further increased by the necessity of preparing those solutions shortly before use, or at times, at the time of use, especially in the case of unstable and difficult to handle allergens. In second place, it is either difficult or even impossible to execute in that manner a homogeneous application of the substance to the skin. It often happens that there are obtained either local overdoses which may cause irritations, or other serious reactions in the patient, or even local insufficient doses which then result in an absence of reaction leading to an erroneous interpretation. Finally, the contours of the skin zone receiving the application of substance often present an irregular shape which may prevent the reading of a positive reaction when said reaction is weak, or which may render difficult an interpretation of the intensity of the reaction.

The classical approach to using dinitrochlorobenzene (DNCB), that is referred to hereinafter, is described by Epstein and Kligman in the "Journal Investigational Dermatology", Vol. 31, pages 103–108. That procedure, now slightly modified, is described by Lynn E. Spitler in "Manual of Clinical Immunology", Chapter 6, pages 56–57.

The disadvantages associated with the classical procedure for using DNCB include, but are not limited to, the following:

1. It is necessary, prior to use, to dissolve a specified amount of DNCB in acetone. Such a step always introduces the possibility for error in calculating the amount of DNCB to be added to a specific amount of acetone. It is well known that preparation of products by a user just prior to use is frowned upon by the Food and Drug Administration. The F.D.A. has a very strong preference for accurately controlled and prepackaged doses supplied by competent manufacturers.

2. The DNCB solution must be kept in a refrigerator and protected from light following preparation. Light is very destructive to DNCB. After two weeks, under the most favorable conditions of storage, the solution of DNCB must be discarded. Freshly prepared DNCB must be made up every two weeks. Another factor related to this particular approach is that acetone evaporates rapidly, and even under the most desirable conditions, the intensity of the dose can change over the two-week period of storage.

3. The individual who is responsible for preparing the DNCB solution can easily be sensitized by an accident in which the solution comes into contact with the skin. Those who prepare DNCB solutions are advised to wear rubber gloves. Even with the rubber gloves, accidental sensitization cannot be prevented.

4. It is not possible to apply the DNCB solution uniformly within the 2-3 cm. diameter of the metal ring. In some cases, the application will be stronger in one area than in another. Consequently, one does not gain uniform administration of DNCB to the complete area of the circle that is approximately 2-3 cm. in diameter. In addition, the DNCB application is not always contained in the area defined by the metal ring. If the DNCB seeps out around the edge of the ring, then an irregular reaction occurs. Reactions range from reasonably well defined circles to poorly defined circles. In some cases, the reaction may be quite irregular.

5. The classical method referred to previously does not provide for good dose control. In some cases, the dose may be too light, and in other cases, it may be to intense, causing burning of the skin. There is no way to insure a uniform administration of dose. Consequently, the dose will vary some from patient to patient.

6. The acetone used in the preparation of DNCB will evaporate rapidly, while the DNCB crystallizes on the skin. This creates difficulty in knowing the amount of DNCB that actually penetrates or migrates into the skin.

7. The nature of the classical method is such that it does not provide an adequate pharmaceutical form that lends itself to precise control, such as chemical analysis and animal safety testing before use. This point relates closely to Point 1.

8. The classical procedure does not allow for a standardized does. This was stated earlier, but not quite in the same terms. A standardized dose will become significant and more clearly understood when we describe in detail the instant invention.

9. The classical procedure is highly inconvenient, both to the administrator and to the patient receiving it. The administrator can and does inadvertently become sensitized by DNCB during the process of administration.

10. The solution of DNCB is highly unstable. Even during the two-week storage period, there can be a substantial variation in the concentration of the solution due to evaporation of acetone. We touched on this subject earlier, but this statement boils it down somewhat more precisely.

The device hereinafter disclosed for applying DNCB as a patch test will include the following advantages:

1. The product is prepared in its final pharmaceutical form by the manufacturer, and not by the user, making possible a very accurate procedure that provides exactly the same product from lot to lot. The manufacturer is able to conduct precise chemical measurements on the product, as well as animal tests for safety.

2. The product is stable and usable at the labeled strength for a period of time exceeding one year when stored under recommended conditions. This long-term stability of the product is an important advantage.

3. The product is packaged in such a way that the DNCB is completely and safely sealed. When carefully administered, there is virtually no chance for the user to become sensitized.

4. The product, by utilizing semi-synthetic glycerides, provides distinct advantages, such as stability in storage for a long period of time, and a uniformly administered dose of DNCB during the period of time that these glycerides slowly melt at the temperature of the skin to which they are exposed or applied. The circular mass of semi-synthetic glycerides provides a homogeneous and uniform administration of DNCB to the entire area of the circle, providing very consistent and uniformly circular reactions. This method eliminates burning of a section of the test site, and having reaction results that are too light at another portion of the site.

5. The Patch Test delivers the DNCB to the skin in a slow and uniform manner so that when the patch is removed, there is no residual crystalline DNCB. With the classical method, one finds at the sensitization site residual crystals of DNCB following the evaporation of acetone. Safely disposing of the residual crystals of DNCB may present a problem.

6. With the herein described product and the method of delivery involving semi-synthetic glycerides, the total dose used for initial sensitization is only 100 mg. With the classical procedure described earlier, the sensitizing dose utilized is 2,000 mg., or a dose twenty times greater than that used with the herein described product. The product provides superior clinical results from a greatly reduced dose, constituting an unexpected result that should create patentability. There have been previous attempts to reduce the dose through the use of vehicles such as corn oil, but these methods have failed to provide the very low, but extremely effective, dose made possible by the new product.

7. On the first visit, the patient is sensitized by the product using a 100 mg. dose. During a second visit, ten to twelve days after the sensitizing dose, the results are read. A very high percentage of patients will exhibit a spontaneous systemic primary reaction referred to as a "spontaneous flare". The product provides a greater incidence of "spontaneous flare" than the classical method or any other methods that have been employed.

8. The method for using the product provides a well defined, circular reaction, while the classical method can provide reactions ranging from well defined to substantially irregular. The reaction from the product tends to be uniform over the entire circular area, while the reaction from the classical method may vary considerably over the area on which DNCB was applied. The well defined circular reaction, with uniformity of surface area, makes the reading of results easier and more accurate.

The present invention has as its purpose to remedy those various drawbacks and to give a patch for skin tests which requires no preparation at the time of use, thus eliminating practically all dangers of contact between the substances and the operator, and further making it possible to apply to the skin a homogeneous (even) amount of substance, accurately dosed and spread over a constant area, this appreciably helping the reading and the interpretation of the reactions.

The present invention also has as its purpose to supply such patches for skin tests which may be kept for a long period of time, while keeping the qualities of the substances to be tested, especially with respect to volatile allergens or those applied in small doses.

The patches according to the present invention indeed make possible an excellent protection of the substances to be tested with respect to external phenomena such as oxidation, the effect of light, humidity, etc. It also makes possible, at least in some cases, the modification of the test application procedure, by causing with sufficient reproducibility spontaneous primary reactions which render useless a second application, as is generally done now. Finally, it also makes it possible to appreciably decrease the doses administered, and consequently the dangers of accident or of slight illness, while ensuring reactions having the desired reproductibility and safety.

The present invention has as its object an adhesive patch for skin tests comprising an adhesive layer on which there is placed, in its central part, a first layer of aluminum sheet or of a similar metal, covered with a synthetic material, with a small plate or patch made of absorbent material and which contains a dose of the test substance, said plate or patch being affixed to the center of said layer, and of a second layer of a sheet of aluminum or of a similar metal, said second layer being sealed to the first one as close as possible to the periphery of the absorbent material.

In a preferred form of execution, the second external layer is preferably provided with a simple and dependable means making its application and its removal possible. The first layer placed between the adhesive sheet and the absorbent material preferably is covered with a synthetic material such as polyethylene, a polyvinyl resin, a polyalkylvinyl resin, polyvinylidene chloride, a polyvinylic copolymer, a polyacrylic copolymer etc . . ., for example. In general it is possible to use all resins or copolymers which are suited to be applied on a sheet of aluminum or of a similar metal. The synthetic material renders possible the sealing of the second external layer on the first one, and it also makes it possible to fix the absorbent material.

By the expression "similar metal" it must be understood according to present invention all metals which are able to be laminated in thin and flexible sheets. Among those metals capable of being use, it is possible to mention in addition to aluminum, tin and lead. The thickness of the metal sheets and more particularly of aluminum sheets is generally of about at least 25 microns.

The absorbent material preferably presents itself in the form of the small plate or round piece of filter paper or of blotting paper, the area of which ranges between 2 and 7 $cm^2$.

The tight (leakproof) sealing between the two layers must be done as close as possible to the periphery, and preferably at the periphery itself of the round piece or plate of absorbent material, so as to avoid all danger of contamination of a part of the first layer by the substance to be tested.

Indeed, if the tight sealing were not executed as close as possible to the periphery of the small disc or plate of absorbent material, it could happen that, through an evaporation or sublimation process, partial condensation of the substance to be tested would take place on the first layer, a situation which would render reading of the reaction difficult because of its non-regular area.

In an especially favored form of execution, the test substance, especially in the case of a substance such as dinitrochlorobenzene, dinitrofluorobenzene or other allergens such a oxazolone, beryllium fluoride or paraphenylenediamine, is mixed with a suitable quantity of an excipient which is more or less solid at room temperature, but capable of softening or of melting when in contact with the skin, without being volatile under heat.

Among those materials capable of being used as excipients, it is possible to mention the glycerides of fatty acids in $C_{12}$–$C_{18}$ and especially the palmitostearic glycerides, the polyoxyethylenated glycerides of fatty acids, the alkyl esters of fatty acids such as the isopropyl myristate or palmitate, the fatty acids, the fatty alcohols in $C_{12}$–$C_{18}$ as well as ethers of said fatty alcohols and the esters of glycols.

There are preferably used, according to the invention, semi-synthetic glycerides, the melting point of which ranges between 33° and 45° C., and especially those sold by the Gattefose Co. under the commercial name of "SUPPOCIRE".

Hydrosoluble excipients may also be used, either alone or mixed with the preceding ones, such as propyleneglycol, glycerin, polyoxyethylenated glycols and alcohols.

Surprisingly, it has been observed that, for example, in the case of a much used allergen such as dinitrochlorobenzene presented in a suitable excipient of that type, it was possible both appreciably to decrease the dose of allergen and systematically to cause a primary spontaneous reaction, making it possible to perform the test in a single application.

Such results are not explained only by the fact that in the patch according to the invention the allergen substance is stabilized before the use of the patch and also while said patch is applied to the skin, but also by an action which facilitates and regularizes the penetration of the skin by the allergen substance.

Thus, in the case of an adhesive dinitrochlorobenzene patch according to the invention, the quantity of allergen substance needed to sensitize the subject preferably ranges between 60 and 150 gammas (1 gamma=1 microgram), the concentration being less than 50 gammas per square centimeter of area of the absorbent material. It is, however, possible, of course, to use more important quantities, but experience proves that it is useless, while in the usual tests doses of at least 300 gammas/cm$^2$ normally are necessary. The most classical technique consists in a total application of 1,000 or even of 2,000 gammas. In the same manner, reaction revealing patches may contain smaller doses, of 1 to 10 gammas, for example, while usually doses of 20 to 50 gammas, and even 100 gammas are necessary.

The invention also has as its object a process for the fabrication, in continuous process, of the adhesive patch, characterized by the fact that there is made to pass by a strip of aluminum or of a similar metal, covered with a synthetic material and meant to constitute the first layer located under the absorbent material; that there are affixed, at regular intervals plates or small round discs of absorbent material to said strip; that there is spread over each small round disc a given quantity of the substance and possibly of its excipient in a solution, that the solvent is evaporated, for example, by causing the strip to run through an air current; that there is brought, on said strip, a second strip which constitutes the second layer; that the two layers are sealed together as close as possible to the periphery of said small round discs, after which there are carried out the various operations of cutting and of connection with a strip of adhesive support, at regular intervals, said strip of adhesive support being then preferably covered with a corrugated strip which protects the adhesive (material) before the individual patches are finally cut out.

According to the present invention, the second layer may be identical with or different from the first one.

The leakproof seal between the two layers preferably is done by heat, the temperature being a function of the nature of the synthetic material used.

In a preferred mode of execution of the invention, in which there are manufactured patches for dinitrochlorobenzene skin tests or of tests with other closely related substances, it is advantageously possible to dissolve the substance and its excipient in a common solvent, for example, in trifluorotrichloroethane or in a mixture of acetone and chloroform.

Other advantages and characteristics of the invention will appear upon reading of the following description, given as an example which is not limitative, and which refers to the attached drawings in which:

BRIEF DESCRIPTION OF THE DRAWINGS

FIG. 1 represents a perspective view from the top of a patch according to the invention with the corrugated layer and the second foil layer partially removed;

FIG. 2 represents a cross-section view of that patch.

DETAILED DESCRIPTION OF THE DRAWINGS

Referring to the drawings, it is seen that the adhesive patch comprises a piece of adhesive cloth 1, of the "Sparadrap" type, the shape of which is generally square, and the edge of which is approximately 6 centimeters long. On the back face of that piece there are placed a certain number of written indications which make it possible clearly to identify the allergen and its concentration. Said piece presents, on the side of its adhesive face, a first layer 2, the general shape of which is a square, the edge of which is approximately 3.5 cm, thus leaving around layer 2 a peripheral strip 3 which will make it possible to maintain the patch applied against the epidermis of the user, establishing a continuous contact all along peripheral zone 3.

Layer 2 is a complex part formed of an aluminum sheet covered on its face that does not adhere to layer 1, with a thin layer of a synthetic material, such as polyethylene, for example, which appears illustrated as a dark line 9 in FIG. 2.

Centrally of the edges of layer 2 there is sealed to the polyethylene layer 9 a circular small piece 4 of absorbent material, the area of which is approximately 3 cm$^2$.

Layer 2 and small disc 4 are both overlaid with an external layer 5 made simply of an aluminum sheet, the area of which is preferably slightly larger than that of layer 2, layer 5 being provided with, on one of its edges, a fold 6 which constitutes a small prehension tongue.

As may be seen in FIG. 1, a circular sealing region 7, carefully executed, secures layer 5 against the layer 2, in order to provide a leakproof continuous seal between the two layers 5 and 2, located as close as possible to the periphery of small disc 4.

The patch according to the invention further is advantageously covered with the usual adhesive protecting layer such as a strip of tarlatane or of corrugated plastic material 8.

To manufacture the patch, according to the invention as described, in a continuous manner, there is first made to pass, continuously or intermittently, a web made of the material constituting layer 2, a web of aluminum-polyethylene complex, for example, a paper-aluminum-polyethylene complex, and there is placed on it, at regular spaced intervals, small round discs of absorbent material, and sealing said small discs, by heat, to the polyethylene or some other equivalent and suitable material of the complex. The web with those small round discs thereon is then made to pass past a test substance distributing station.

In the case of a dinitrochlorobenzene patch, the test substance distributing station advantageously contains a dinitrochlorobenzene and excipient solution, for example a "Suppocire", in trifluorotrichloroethane, or in a 50—50 acetone and chloroform mixture. The distributing station is planned so that there is deposited on each small disc a dose of test solution. In the case of 3 cm$^2$ filter paper discs capable of absorbing 40 microliters of liquid, each 40 microliter dose contains 100 gammas of dinitrochlorobenzene and 4 mg of Suppocire. Once the dose has been deposited on the small absorbent disc, the web runs through a hot or cold air current to evaporate the solvent. A sheet of aluminum is placed over the web fitted with the small discs which have now absorbed test solution and said aluminum sheet is sealed to the web in circular heat-sealed regions 7 surrounding each small disc.

After that operation, the resulting complex is cut into pieces preferably, each piece having positioned at its center the small disc protected in a leakproof manner. Each piece is then placed, at regular intervals, on a strip of Sparadrap, and a protective corrugated covering is applied to the adhesive side of the Sparadrap. The complex is cut regularly at approximately every 6 centimeters to obtain the patch depicted in the drawings. Printing of the required legal indicia on each patch may be accomplished either before or after the cutting procedure.

There is thus obtained a patch for skin tests wherein the test substance is ready for use, accurately dosed, and stable and homogeneously distributed on the absorbent discs. The patch is easy to handle without danger of operator sensitization, or of error in the user's dosage.

The comparison between the application of the patch according to the invention, using dinitrochlorobenzene, and the classical techniques, showed the advantages secured by the invention, and is again summarized below.

The results of the tests performed by means of the patch of the present invention can be perfectly reproduced. It is possible to read the test without ambiguity. The reaction of the skin treated by the round disc, uniformly coated with the test substance, cannot be confused with irritation caused by the Sparadrap. The reading does not extend beyond the diameter of the small disc, and no local overdose is possible.

Moreover, the test requires a dose much smaller than in the prior art. Especially sensitization test results are systematically obtained with a 100 gamma dose, while doses of 2,000 gammas are common when using the classical approach. In the same manner, sensitization is accomplished with 5-to-10 gamma doses instead of the 50-to-100 gamma doses necessary with the classical approaches.

The test procedure also is simplified, as shown by the following comparisons:

1. Classical test: In the classical test the patient is sensitized by directly depositing on the skin a few drops of an acetone solution including 1,000–2,000 gammas. After evaporation of the solvent, a protective bandage is applied over the area of deposit. The patient may remove the protective bandage himself, after 24 hours. Two to three weeks later, the patient returns, and a check is made for a possible spontaneous primary reaction. There generally is none, and there is again deposited a single dose of 100 gammas, or variable doses (100, 50, 20 gammas) to reveal the sensitized state. A third visit of the patient is then necessary, 24 to 48 hours later, for further reading of the reaction.

2. Test According to the Invention: At the time of the first visit, a 100 gamma patch, fashioned in accordance with the present invention, is applied, and 24 hours later the patient removes the patch. A second visit takes place 10 to 12 days after the application of the test patch to read the result. The reading may take place immediately because of a spontaneous primary reaction (spontaneous flare, as used by English writers) which is systematic.

It is, of course, possible, when desired, to complete the immunological investigation by applying a revelation test dose of 1-to-10 gammas.

What we claim is:

1. In a patch test for administration of a standardized, precise dose, of reactive material to skin to determine sensitivity to said reactive material; the improvement comprising, in combination:
   a first metal foil layer laminated on the inner side thereof with a layer of synthetic impermeable material,
   an absorbent disc means, containing a dose of a test substance, positioned on said layer of synthetic material spaced inwardly of the edges of said first metal foil layer,
   a second metal foil layer overlying the absorbent disc means and being heat sealed to the layer of synthetic material on said first metal foil layer by a continuous peripheral heat seal located substantially immediately adjacent the peripheral edge of the absorbent disc means, to provide a sealed pouch means for protecting the dose of test substance in the absorbent disc means from light and also against leakage of the dosage of the test substance in the absorbent disc means beyond said heat seal adjacent the absorbent disc means.

2. A patch according to claim 1, wherein the test substance is mixed with an excipient.

3. A patch according to claim 2, wherein the excipient comprises at least one compound selected from the group consisting of: the glycerides of fatty acids in $C_{12}$–$C_{18}$, the polyoxyethylenated glycerides of fatty acids, the alkyl esters of fatty acids, the fatty acids, the fatty alcohols in $C_{12}$–$C_{18}$, the ethers of said fatty alcohols and the esters of glycols.

4. A patch according to claim 2, wherein the excipient is a semi-synthetic glyceride having a melting point ranging between 33° and 45° C.

5. A patch according to claim 2, wherein the excipient comprises at least one compound selected from the group consisting of propylene glycol, glycerine, the polyoxethylenated glycols and alcohols.

6. A patch according to claim 1, wherein the test substance is an allergen.

7. A patch according to claim 6, wherein the allergen is a compound selected from the group consisting of dinitrochlorobenzene or dinitrofluorobenzene.

8. A patch according to claim 6, wherein the quantity of allergen is at least equal to 60 gammas and constitutes a sensitizing patch.

9. A patch according to claim 8, wherein the quantity of allergen is less than 150 gammas.

10. A patch according to claim 6, wherein the quantity of allergen ranges between 1–10 gammas and constitutes a revelation patch.

11. A patch test according to claim 1, wherein the synthetic impermeable material is selected from one group consisting of polyethylene, a polyvinyl resin, a polyalkylvinyl resin, polyvinylidene chloride, a polyvinylic copolymer and a polyacrylic copolymer.

12. A patch according to claim 1, wherein the absorbent disc means is formed from a material selected from the group consisting of filter paper and blotting paper.

13. A patch according to claim 1, wherein the area of the absorbent material ranges between 2–7 cm$^2$.

14. A patch according to claim 1, wherein the second foil layer presents a small tab.

15. A patch test as in claim 1 wherein the patch test is packaged for adhesive application by securing the first metal foil layer centrally to an adhesive strip, leaving portions of the adhesive strip adjacent the first metal foil layer exposed, and a protective corrugated covering is applied to the exposed portions of the adhesive strip and covers and encloses the second metal foil layer.

16. A patch test as in claim 1 wherein the metal of both metal foil layers is from the group consisting of aluminum, tin and lead.

17. A patch test as in claim 16 wherein the metal of both metal foil layers is aluminum sheet of about 25 microns thickness.

* * * * *